US007776571B2

(12) United States Patent
Mahant et al.

(10) Patent No.: US 7,776,571 B2
(45) Date of Patent: Aug. 17, 2010

(54) MULTI-SUBSTRATE BIOCHIP UNIT

(75) Inventors: Vijay K. Mahant, Murrieta, CA (US); Fareed Kureshy, Del Mar, CA (US); Shailendra Singh, Calsbad, CA (US)

(73) Assignee: Autogenomics, Inc., Carlsbad, CA (US)

( * ) Notice: Subject to any disclaimer, the term of this patent is extended or adjusted under 35 U.S.C. 154(b) by 431 days.

(21) Appl. No.: 10/495,554

(22) PCT Filed: Jan. 24, 2002

(86) PCT No.: PCT/US02/03917

§ 371 (c)(1), (2), (4) Date: Jun. 10, 2004

(87) PCT Pub. No.: WO03/050591

PCT Pub. Date: Jun. 19, 2003

(65) Prior Publication Data

US 2004/0224318 A1 Nov. 11, 2004

Related U.S. Application Data

(63) Continuation-in-part of application No. 09/735,402, filed on Dec. 12, 2000, now abandoned.

(51) Int. Cl.
*C12M 1/00* (2006.01)
*G01N 15/06* (2006.01)
*G01N 33/549* (2006.01)

(52) U.S. Cl. ................. 435/174; 435/283.1; 435/287.8; 436/528; 422/68.1; 422/82.05

(58) Field of Classification Search ..................... 435/6, 435/7.1, 174, 283.1, 287.2; 422/68.1, 82.05
See application file for complete search history.

(56) References Cited

U.S. PATENT DOCUMENTS 4,704,255 A * 11/1987 Jolley ......................... 422/101
4,968,602 A * 11/1990 Dattagupta ..................... 435/6
5,250,443 A * 10/1993 Lindholm et al. ........... 436/529
5,545,531 A * 8/1996 Rava et al. ..................... 435/6

(Continued)

FOREIGN PATENT DOCUMENTS

EP 0874242 10/1998

(Continued)

OTHER PUBLICATIONS

Sgima-Aldrich website catalog www.sigmaaldrich.com.*

(Continued)

*Primary Examiner*—BJ Forman
(74) *Attorney, Agent, or Firm*—Fish & Associates, PC

(57) ABSTRACT

An analytical device has a housing that encloses a multi-substrate chip having a reference marker and a plurality of substrates, wherein the housing is configured such that the reference marker and the substrates are illuminated by respective light sources at different angles. Further contemplated analytical devices include a housing with a cavity in which a multi-substrate chip having a plurality of substrates is at least partially disposed, wherein at least one of the plurality of substrates is coupled to a carrier via a crosslinker that is disposed in a matrix.

18 Claims, 3 Drawing Sheets

U.S. PATENT DOCUMENTS

| | | | | | |
|---|---|---|---|---|---|
| 5,578,832 | A | * | 11/1996 | Trulson et al. | 250/458.1 |
| 5,599,695 | A | | 2/1997 | Pease et al. | |
| 5,605,662 | A | | 2/1997 | Heller et al. | |
| 5,631,734 | A | | 5/1997 | Stern et al. | |
| 5,632,957 | A | | 5/1997 | Heller et al. | |
| 5,763,870 | A | * | 6/1998 | Sadler et al. | 250/201.2 |
| 5,832,165 | A | | 11/1998 | Reichert et al. | |
| 5,843,655 | A | | 12/1998 | McGall | |
| 5,849,486 | A | | 12/1998 | Heller et al. | |
| 5,911,000 | A | * | 6/1999 | Shen | 382/134 |
| 6,215,894 | B1 | * | 4/2001 | Zeleny et al. | 382/133 |
| 6,225,109 | B1 | * | 5/2001 | Juncosa et al. | 435/288.5 |
| 6,232,066 | B1 | * | 5/2001 | Felder et al. | 435/6 |
| 6,238,869 | B1 | * | 5/2001 | Kris et al. | 435/6 |
| 6,277,628 | B1 | | 8/2001 | Johann et al. | |
| 6,306,348 | B1 | * | 10/2001 | Havens et al. | 422/68.1 |
| 6,312,960 | B1 | | 11/2001 | Balch et al. | |
| 6,337,212 | B1 | * | 1/2002 | Nagle et al. | 436/174 |
| 6,399,394 | B1 | * | 6/2002 | Dahm et al. | 436/180 |

FOREIGN PATENT DOCUMENTS

| | | | |
|---|---|---|---|
| WO | WO 00/04390 | | 1/2000 |
| WO | WO 00/53310 | | 9/2000 |
| WO | WO 00/73504 | * | 12/2000 |

OTHER PUBLICATIONS

Syvanen et al "Fast quantification of nucleic acid hybrids by affinity-based hybrid collection" Nucleic Acids Research, 1986, 14(12): 5037-5048.*

* cited by examiner

MULTI-SUBSTRATE BIOCHIP UNIT

This application is a continuation-in-part application of U.S. patent application Ser. No. 09/735,402, filed Dec. 12, 2000 now abandoned, and also claims priority to PCT Application entitled Improved Biochip filed on Dec. 11, 2001 (inventors are Vijay K. Mahant and Fareed Kureshy) which are incorporated by reference herein.

FIELD OF THE INVENTION

The field of the invention is analytic devices and methods.

BACKGROUND OF THE INVENTION

Genomics and proteomics research made a vast number of nucleotide and peptide sequences available for analysis. Consequently, high-throughput screening of samples for the presence and/or quantity of a vast number of known genes or polypeptides has gained considerable interest in recent years. There are various devices and methods known in the art, and many of those devices and methods are adapted for screening of multiple nucleic acid sequences.

For example, in a relatively simple approach, Johann et al describe in U.S. Pat. No. 6,277,628 a test system in which a plurality of carrier structures is enclosed in a capillary, and wherein at least some of the carrier structures (e.g., glass beads) are covalently coated with a biomolecular probe. Johann's system advantageously reduces the ratio of sample volume to test surface, thereby reducing potential delays due to kinetic effects. However, various problems arise with the use of such systems. Among other disadvantages, optical detection (e.g., fluorescence) of a signal from a hybridized probe is at least to some degree impaired by inadvertent absorption of light (e.g., excitation and emission) by the capillary. Furthermore, intrinsic optical effects (e.g., auto-fluorescence) of the capillary will likely further reduce sensitivity of the assay or method. Still further, inadvertent focusing/diffusion of incident and/or emitted light is almost unavoidable due to the strong curvature of the capillary. Moreover, assembly of Johann's test systems is relatively tedious and time consuming.

In another example, hybridization of target molecules from a sample to an immobilized capture probe is accelerated by electrophoretic assistance using a microchip-type device as described in U.S. Pat. Nos. 5,632,957, 5,605,662, and 5,849,486. Use of such microchip devices not only increases the speed of molecular association between a target molecule and a capture probe, but also allows addressability of each "pixel" of the test array. Furthermore, stringency may be electronically regulated in a relatively simple manner in a reverse process to electrophoretically assisted hybridization. However, the sample density of such devices in many commercially available systems is typically limited to about 100 pixels per device. Moreover, electrophoretically assisted hybridization requires use of complex and relatively expensive chips, and loading/hybridization and detection are typically performed using separate instruments, thereby further increasing initial, operating, and maintenance expenses.

In a further example, test arrays are produced using a photolithographic process, thereby allowing relatively high density of capture probes (e.g., greater than 10000 probes per array). Systems for such high-density arrays are described, for example, in U.S. Pat. Nos. 5,599,695, 5,843,655, and 5,631,734. While high-density arrays are particularly useful for sequencing or complex genetic analysis, numerous disadvantages remain. For example, custom synthesis of such high-density arrays is likely cost-prohibitive for all but a few individuals and/or organizations. Furthermore, high-density arrays will often have limited applications in routine clinical diagnostics. Moreover, due to the particular chemistry employed in building such arrays, non-nucleic acid probes (e.g., receptors, antibodies, and other polypeptides) are difficult, if at all, to implement.

Thus, although numerous multi-substrate arrays are known in the art, all or almost all of them suffer from one or more disadvantage (e.g., high cost, difficult to customize, specialized chemistry, etc.). Therefore, there is still a need to provide improved multi-substrate array devices and methods.

SUMMARY OF THE INVENTION

The present invention is directed to an analytical device that includes a housing having a cavity, wherein a multi-substrate chip at least partially disposed in the cavity, and wherein contemplated multi-substrate chip have reference marker and a plurality of substrates in predetermined positions with at least one of the plurality of substrates being coupled to a carrier via a crosslinker that is disposed in a matrix. Particularly preferred devices include a housing that is configured such that the reference marker and the substrates are illuminated by respective light sources at different angles.

In one aspect of the inventive subject matter, contemplated cavities further include a liquid manipulation port, wherein the cavity has preferably a volume of between 0.01 ml and 1 ml. Still further preferred devices include an overflow compartment, which may further include an overflow liquid manipulation port, wherein the cavity is in fluid communication with the overflow compartment when the cavity contains a liquid in a volume that is greater than a predetermined volume of the cavity.

In another aspect of the inventive subject matter, contemplated devices may comprise a second multi-substrate chip at least partially disposed-in the cavity, or a second cavity and a second multi-substrate chip that is at least partially disposed in the cavity.

In alternative aspects of the inventive subject matter, the cavity is formed by the housing and a base element, wherein the multi-substrate chip is coupled to the base element (which is preferably configured to transfer thermal energy and/or ultrasound energy to at least one of the multi-substrate chip and a fluid). In further contemplated aspects, one or more of the substrates are contacted with a sample fluid, a reagent fluid, a wash fluid, and/or a detection fluid when the multi-substrate chip is in a substantially horizontal position, it is further preferred that binding of an analyte to a substrate is also detected while the multi-substrate chip is in a substantially horizontal position.

In still further contemplated aspects, the multi-substrate chip and/or the housing include a reference marker that is automatically readable, and contemplated matrices will further include at least one additive selected from the group consisting of a buffer, a humectant, a light blocking agent, and a surfactant. Suitable matrices may include a single layer, or the matrix maybe formed from at least two chemically distinct layers. A plurality of contemplated analytical devices may be stored in a magazine, preferably such that the base element of the first device is above the housing of the second device.

Various objects, features, aspects, and advantages of the present invention will become more apparent from the following detailed description of preferred embodiments of the invention, along with the accompanying drawing.

DETAILED DESCRIPTION

Figure 1A:
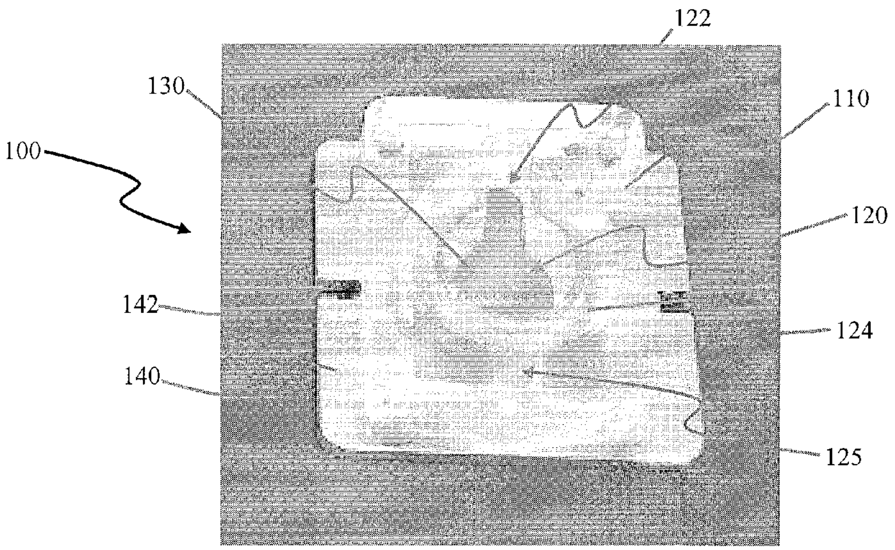
FIG. 1A is a perspective view of an exemplary multi-substrate test device.

The inventors have discovered that a multi-substrate test device may be fabricated in a conceptually simple and cost effective manner. Moreover, particularly, contemplated multi-substrate test devices allow simple customization of the array, fast read-out times, significantly reduced photobleaching of fluorophores, and the substrates are not limited to a particular group or class of biomolecules.

As used herein, the term "multi-substrate" refers to a plurality of chemically and/or physically distinct molecules, wherein the number of such molecules is generally between two and several ten thousand molecules, more typically between hundred and several thousand, and most typically between one hundred and one thousand. Contemplated substrates include biological (i.e., naturally occurring) and non-biological (i.e., synthetic) molecules, wherein especially contemplated biological molecules include nucleic acids (e.g., DNA, mRNA, hnRNA, snRNA, etc.), polypeptides (e.g., enzymes, receptors, antibodies, cytokines, structural proteins, etc.), lipids (membrane lipids, messenger lipids, lipoprotein-bound lipids, etc.), carbohydrates (e.g., glycocalix carbohydrates, glycogen, etc.), and all combinations and/or fragments thereof As further used herein, the terms "first angle" and "second angle" refer to an angle formed between the surface of the (matrix of the) multi-substrate chip and the incident light beam where the incident light beam is either focused or a laser beam. Where the incident light is diffuse or diffracted, the angle is formed between a straight line between the surface of the (matrix of the) multi-substrate chip and the portion of the light emitting device closest to the surface of the (matrix of the) multi-substrate chip, wherein the light emitting device is a light bulb, light-emitting diode, arc, or electroluminescent source.

Examples for non-biological molecules include synthetic nucleic acids, which may further include modified nucleosides or nucleotides (e.g., DNA, MRNA, hnRNA, snRNA, etc.), natural and synthetic polypeptides, which may further include modified amino acids (e.g., enzymes, receptors, antibodies, cytokines, structural proteins, etc.), synthetic lipids (membrane lipids, messenger lipids, lipoprotein-bound lipids, etc.), synthetic carbohydrates (e.g., glycocalix carbohydrates, glycogen, etc.), and all combinations and/or fragments thereof.

The term "chip" as used herein refers to a carrier that has a plurality of substrates in predetermined positions, wherein at least one of the substrates is coupled to the carrier via a crosslinker that is disposed in a matrix. Particularly contemplated multi-substrate chips are described in commonly-owned and copending U.S. patent application Ser. No. 09/735,402, filed Dec. 12, 2000, and priority PCT Application entitled Improved Biochip filed on Dec. 11, 2001 (inventors are Vijay K. Mahant and Fareed Kureshy) which is incorporated by reference herein.

As still further used herein, the term "predetermined position" of a substrate refers to a particular position of the substrate on the chip that is addressable by at least two coordinates relative to a reference point on the chip, and particularly excludes a substantially complete coating of the chip with the substrate. Therefore, preferred pluralities of predetermined positions will include an array with a multiple rows of substrates forming multiple columns (e.g., each substrate has a x-coordinate and a y-coordinate, with x and y greater than 1).

An exemplary multi-substrate test device 100 is depicted in FIG. 1A. The test device 100 has a housing 110, in which a cavity 120 is formed. Cavity 120 typically has a volume of between about 0.01 ml and 10 ml. A liquid manipulation port 122 is in fluid communication with the cavity 120, and the cavity is further partially surrounded by overflow compartment 124 that receives liquid from the cavity when the cavity contains liquid in a volume that is greater than the volume of the cavity. The overflow liquid manipulation port 125 is disposed on the opposite side of the liquid manipulation port 122 and in fluid communication with the overflow compartment 124. A multi-substrate chip 130 is coupled to base element 140, which forms together with the housing 110 the cavity 120. Base element 140 further includes a guide element 142 on at least two sides.

Figure 1B:
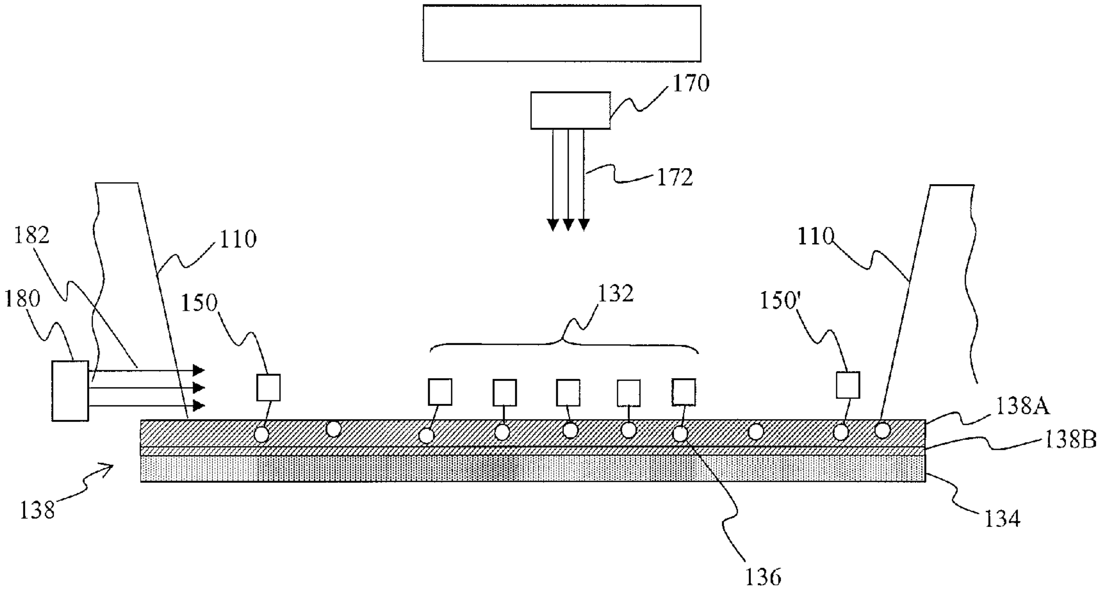
FIG. 1B is a schematic vertical cross-sectional view of a portion of the multi-substrate test device of FIG. 1A.

FIG. 1B depicts a schematic vertical cross-sectional view of a portion of the multi-substrate test chip in which a matrix 138 (comprising a first layer 138A and a second layer 138) is coated onto a carrier 134. Embedded within the first layer 138A of matrix 138 is a plurality of crosslinkers 136 to which a plurality of substrates 132 are coupled (here: via molecular tethers (lines between crosslinkers and substrates)). Also disposed in a predetermined position on the matrix is an reference marker 150 and 150', which are also coupled via a crosslinker (and molecular tether) to the first layer of the matrix.

With respect to the housing 110, it is generally preferred that the housing is manufactured from a transparent high-density polyethylene. However, it should be appreciated that the material for the housing may vary considerably, and alternative materials include natural and synthetic polymers, metals, ceramics, glass, pressed paper, and any reasonable combination thereof. For example, where it is preferred that the housing is disposable, various synthetic polymers and/or pressed paper are considered particularly suitable. On the other hand, and especially where the housing will be reused several times, more durable materials (e.g., ceramics or metal) may be advantageously employed. Furthermore, contemplated materials may also included to allow certain processing steps that would otherwise damage the housing. For example, where the housing needs to be sterilized (e.g., by radiation or autoclaving), glass may advantageously be employed as a housing material.

Similarly, optical characteristics need not necessarily be limited to a transparent material. For example, where desired a reflective or light absorbing material may be employed to improve assay sensitivity. Furthermore, the housing may (by itself or in combination with the base element) be employed to transfer energy to and from the sample. For example, the base portion of the housing may be employed as a transducer for ultrasound energy, while the remainder of the housing may be adapted to heat and/or cool the sample disposed in the housing.

However, it is especially preferred that at least a portion of the housing comprises a clear, semi-transparent, or translucent (i.e., light-permeable) portion that allows incident light to pass through the housing. Such housings are particularly desirable where the multi-substrate chip includes a reference marker and at least one light substrate. Thus, especially preferred devices comprise a housing at least partially enclosing a multi-substrate chip that includes a reference marker and a plurality of substrates in predetermined positions, wherein the reference marker is illuminated by a first light source (180) at a first angle (182), and wherein at least one of the plurality of substrates is illuminated by a second light source (170) at a second angle (172), and wherein the housing is configured such that the first angle and the second angle are not identical.

It should be especially appreciated that separate illumination of a reference marker and a substrate will have numerous advantages. For example, known optically analyzed micro arrays typically require that the focal plane or focal point for detection of a labeled analyte must be independently determined for each of the labeled analytes bound to the micro array, which almost always necessitates illumination of the fluorescent marker of the analyte. Consequently, and especially where the adjustment to the optimal focal plane or point is relatively slow (typically up to about one minute per spot), photobleaching (and concomitantly loss of actual signal) of the fluorophor is all but inevitable. Moreover, individual focal adjustments tend to increase analysis time dramatically, especially where the density of the labeled analytes is relatively high.

In contrast, contemplated devices employ a light source that illuminates one or more reference spots through the housing wherein the illumination light is preferably at least 20 nm different from the illumination light of the substrates. Especially contemplated configurations provide a darkfield illumination of the reference spots. Thus, the intensity of the illumination light of the reference spots may be significantly reduced, thereby reducing the likelihood of photobleaching of labeled analytes bound to the substrates.

Moreover, where the reference marker(s) are in predetermined position relative to the substrates, illumination of the reference marker may be employed to direct the multi-substrate chip into the focal plane of an optical instrument that acquires the optical signal from labeled analytes coupled to the substrates on the multi-substrate chip. Consequently, it is contemplated that refocusing for each of the subsequent pixels in the multi-substrate chip may be partially, if not entirely avoided, thereby significantly reducing measurement time for the entire multi-substrate chip. Determination of the correct focal plane may be provided by acquisition of more than one reference marker, and it is especially contemplated that each multi-substrate chip includes at least four reference markers.

While it is generally preferred that the entire housing is completely light-permeable, it should also be appreciated that only portions (e.g., channels through the housing with or without lenses) may be light-permeable for illumination of the reference markers. Alternatively, and especially where the housing is light-impermeable, it is contemplated that the reference markers are illuminated with conventional darkfield illumination, or in an illumination in which the reference marker is illuminated by a first light source at a first angle, and wherein at least one of the plurality of substrates is illuminated by a second light source at a second angle (preferably with a difference in angle of greater than 45 degrees).

Suitable reference markers include all known molecules or compositions that produce an optically detectable signal (i.e. light emission or absorption) upon illumination. Therefore, all known chromophores and fluorophores are especially contemplated. Furthermore, it should be appreciated that the reference marker may also include a chemiluminescent portion that emits an optically detectable signal under predefined reaction conditions. Such reaction conditions may, for example, be generated by addition of suitable reagents to the cavity of the device and are well known to a person of ordinary skill in the art.

Especially preferred light sources include various lasers, however, it is generally contemplated that all light sources known for photon excitation (e.g., fluorescence, phosphorescence) are suitable for use herein. There are numerous suitable light sources known in the art, and a exemplary collection of such sources may be found in Fluorescence Methods and Protocols (Methods in Molecular Biology) by Dan Sackett (Humana Press; ISBN: 0896035441), or Fluorescence Microscopy and Fluorescent Probes by Jan Slavik (Plenum Pub Corp; ISBN: 0306460211). However, it is particularly preferred that where lasers are employed that the difference in wavelength between the first and second laser (for illumination of reference marker and substrate) is at least 20 nm.

Still further, suitable housings and/or multi-substrate chips may include one or more registration markers, barcodes, and/or standards that may be read manually or automatically. For example, it is contemplated that manually readable markers include imprinted or otherwise affixed serial numbers, type of substrates on the chip, supplier telephone numbers, etc. Automatically readable reference markers may include bar codes or one or more colored or fluorescent tags that may encode a particular piece of information.

With respect to the size of the housing, it is contemplated that a particular size is not limiting to the inventive subject matter. However, preferred sizes are typically sizes in which the longest dimension of the housing is less than 10 inches, more preferably less than 5 inches, even more preferably less than 2 inches, and most preferably 1 inch and even less.

Consequently, it is contemplated that the volume of suitable cavities may vary considerably. However, preferred cavities will have a volume of less than 20 ml, more preferably between 0.01 ml and 1 ml, and most preferably between 0.01 ml and 1 ml. With respect to the shape of suitable cavities it is contemplated that any reasonable shape will be appropriate so long as such shape will accommodate the multi-substrate chip at least in part. For example, suitable cavities may have a round, elliptical, or square shape. Similarly, the walls of the cavity may be perpendicular to the surface of the multi-substrate chip or in any angle (preferably between 45 degrees and 89 degrees). Therefore, depending on the size and configuration of the cavity, the wall(s), and the multi-substrate chip, it is contemplated that the multi-substrate chip may be located in various positions of the cavity. However, it is generally preferred that the multi-substrate chip is disposed at the bottom of housing (which may or may not be a base element). Alternatively, however, the multi-substrate chip may also be attached to the housing such that the multi-substrate chip will be in a position other than at the bottom of the cavity (e.g., suspended from the walls of the cavity).

It is still further contemplated that the cavity may be in fluid communication with one or more liquid manipulation ports, wherein such ports may be configured to receive a pipette tip for addition and/or removal of fluids. Alternatively, contemplated liquid manipulation ports may also be channels or through-holes in the housing to add and/or drain a fluid. While not especially preferred, contemplated liquid manipulation ports may further include reservoirs that retain reagents or other test related fluids, or provide structures to increase/ decrease non-linear flow of a liquid, or structures to accelerate or decelerate flow of a liquid, or structures to mix a fluid with another fluid.

In a further preferred aspect of contemplated devices, the cavity is in fluid communication with an overflow compartment, and it is especially preferred that the cavity is in fluid communication with the overflow compartment only when the cavity contains liquid in a volume that is greater than the predetermined volume of the cavity. Thus, contemplated overflow compartments may comprise a channel or a through-hole positioned such that fluid is only received from the cavity when the level of the fluid reaches a predetermined height. Additionally, suitable overflow compartments may include one or more overflow liquid manipulation ports, and the same considerations as for the liquid manipulation port(s) as described above apply for contemplated overflow liquid manipulation ports. In a particularly preferred aspect, the overflow compartment is a channel that at least partially surrounds the cavity and includes at least one overflow liquid manipulation port.

In a further particularly preferred aspect of the inventive subject matter, the multi-substrate chip is disposed at or near the bottom of the cavity and the cavity is in fluid communication with an overflow compartment only when the cavity contains liquid in a volume that is greater than the predetermined volume of the cavity. Viewed from another perspective, it should be especially recognized that in such devices the volume of a fluid in the cavity may be maintained at a constant value without prior determination of the amount of fluid that is already in the cavity. A constant volume of fluid is particularly desirable where illumination of a sample, or detection of an optical signal from the multi-substrate chip is performed through a layer of a fluid, since the height of the fluid layer is predetermined and substantially constant (i.e., changes typically less than +/−5%, more typically less than +/−2%) in such cavities.

Figure 4:
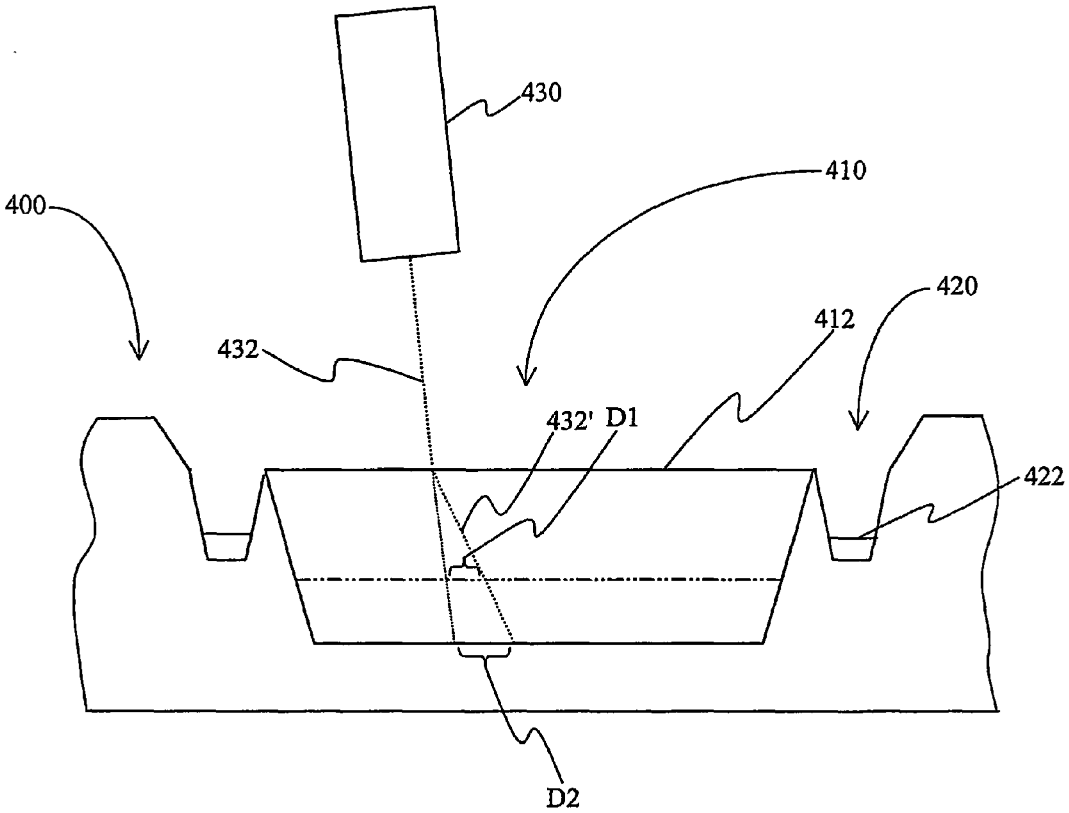
FIG. 4 schematically illustrates illumination of an exemplary multi-substrate test device having an overflow compartment.

FIG. 4 illustrates some of the advantages of contemplated cavities that are in fluid communication with an overflow compartment. Here, a multi-substrate test device 400 has a cavity 410 in fluid communication with the overflow compartment 420 (when the fluid volume in the cavity exceeds the volume of the cavity). Laser beam 432 from laser. 430 (typically from a confocal microscope; not shown) is deflected at cavity fluid surface 412. The angle of deflection is predominantly determined by the refractive index of the fluid and the angle of laser beam 342 relative to the surface 412. Regardless of the angle, however, it should be appreciated that the horizontal deviation D1 and D2 will, among other things, be determined by the length of the path that the light will travel through the fluid. Thus, a predetermined volume of the cavity (and therefore a predetermined height of the fluid) will significantly reduce, if not entirely eradicate misillumination of positions on the multi-substrate chip. Moreover, providing a constant fluid volume over the multi-substrate chip will circumvent most of the problems with attempts to remove fluid prior to detection of an optical signal (e.g., incomplete draining, entrapped air bubbles, etc.).

In a further preferred aspect of contemplated devices, the cavity is formed at least in part by the housing and a base element, and it is especially contemplated that the housing and the base element are removably coupled to each other (e.g., via pins, screws, etc.). However, in alternative aspects, the housing may also be permanently coupled to the base element. Thus, the multi-substrate chip in at least some of the preferred devices may be coupled (directly or indirectly) to the base element. Direct coupling means that the carrier of the multi-substrate chip is attached to the base element, whereas indirect coupling means that there is at least one additional layer between the multi-substrate chip and the base element.

In yet further preferred aspects, the cavity is an open cavity, wherein the term “open cavity” as used herein refers to a cavity in the housing that is accessible from a point outside the housing without passing through a wall of the housing or without passing through a channel that connects the cavity with the outside of the housing.

With respect to the material of the base element, it is contemplated that any material suitable for (a) supporting the multi-substrate chip and (b) attaching the base element to the housing is considered suitable for use herein. However, it is generally preferred that the base element comprises a material (and is configured) to transfer thermal and/or ultrasound energy to the multi-substrate chip and/or a fluid in the cavity. Consequently, particularly preferred materials include metals (e.g., aluminum), ceramics, and synthetic polymers.

While not limiting to the inventive subject matter, it is generally preferred that the base element has at least one, more preferably two guide elements that will assist in automated handling of contemplated analytical devices. For example, contemplated guide elements include indentations or protrusions from the base element, but may also include magnetic spots or elements engaging with an actuator (e.g., hooks, loops, etc.). Thus, contemplated devices may comprise a housing with a first width and a base element with a second width, wherein the first width is smaller than the second width.

Figure 2A:
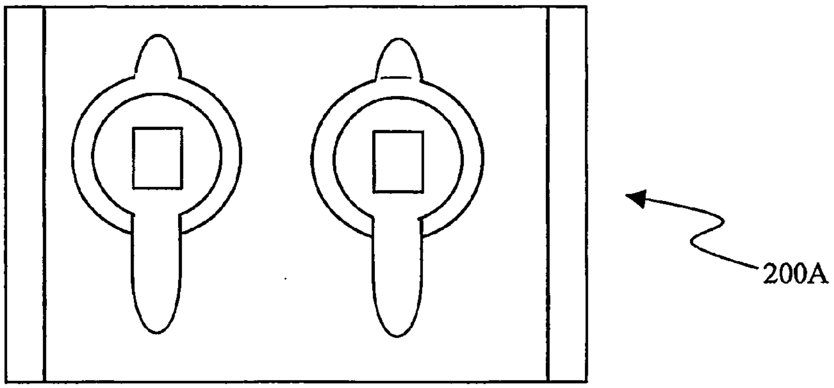
FIG. 2A is a schematic top view of one alternative multi-substrate test device.
Figure 2B:
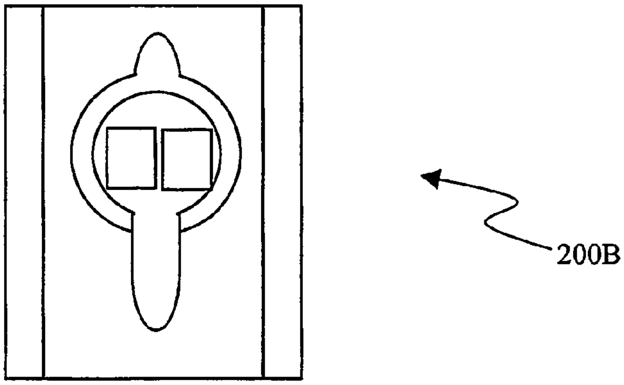
FIG. 2B is a schematic top view of another alternative multi-substrate test device.

In yet further alternative configurations, suitable analytic devices may include more than one multi-substrate chip (with at least one chip being at least partially disposed in the cavity). For example, where cell extracts are analyzed in such devices, a first multi-substrate chip may be employed to analyze a nucleic acid population while a second multi-substrate chip may be employed to analyze a polypeptide population (see FIG. 2B). Alternatively, and especially where hybridization conditions vary between or among multiple multi-substrate chips, multiple cavities and with multiple multi-substrate chips may be employed (e.g., with one chip per cavity), wherein at least one of the chips is at least partially disposed in the respective cavity (see FIG. 2A).

Preferred matrices are multi-functional matrices that include in addition to the crosslinker at least one further additive that is specific to a particular configuration or test condition. Suitable additives may impart selected characteristics and especially contemplated additives include a buffer (e.g., to adjust stringency to a particular level, to modify pH to a particular value, etc.), a humectant (e.g., to maintain or adjust matrix hydration), a light blocking agent (e.g., to suppress carrier autofluorescence), or a surfactant (e.g., to improve matrix adhesion to the carrier).

Furthermore, suitable matrices may include multiple layers, which are preferably chemically distinct layers. For example, a first layer may include a detergent to improve adhesion to the carrier, while a second layer may include a light blocking agent to reduce carrier autofluorescence, and a third layer includes the crosslinker that is employed to couple the substrate to the carrier. It is generally contemplated that any crosslinker is suitable that retains (covalently or non-covalently) a modified or unmodified substrate, it is particularly preferred that the crosslinker comprises a molecule that binds biotin with a $K_D$ of no greater than $10^{-5}$M. Thus, suitable crosslinkers include avidin, streptavidin, and antibodies against biotin. Furthermore, it is contemplated that suitable crosslinkers in the matrix may also be employed to bind a reference marker or reference substance against which position or amount of optically detected signal may be calculated.

Moreover, it should be especially appreciated that in preferred aspects the matrix (e.g., agarose, gelatin, or polyacrylamide) is coated onto the carrier by methods well known in the art. Therefore, problems associated with uneven carrier surfaces are generally avoided. Furthermore, by addition of additives, undesirable signal interference from the carrier can be substantially reduced, if not eliminated.

Figure 3:
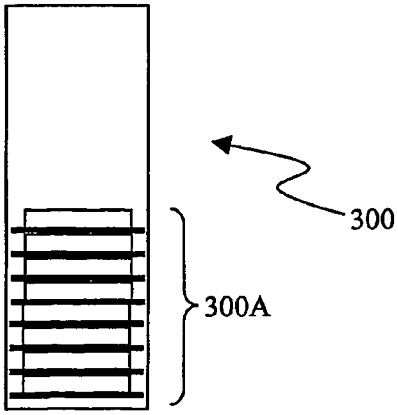
FIG. 3 is a schematic side view of a magazine including a plurality of multi-substrate test devices.

In yet another aspect of the inventive subject matter, it should be appreciated that a plurality of contemplated analytical devices may be included into a magazine to facilitate reloading of an analyzer with a number of multi-substrate chips. While the arrangement of the analytical devices in the magazine may vary considerably (e.g. linear as a band or chain of devices, two-dimensional as an array of devices, or three-dimensional as a roll of devices), it is generally preferred that contemplated devices are stacked such that a base element of a first device is disposed above a housing of a second device. A guide in a magazine may engage with a guide element in contemplated devices, and a weight or a spring on top of the devices may provide the mechanical force to sequentially advance the devices to the bottom of the magazine. An exemplary magazine is depicted in FIG. 3, in which the magazine 300 includes a plurality of analytical devices 300A.

In operation, an analytical device according to the inventive subject matter is provided (e.g., in a magazine, or manually-inserted into an analyzer), and in one step, the plurality substrates is contacted with at least one fluid selected from the group consisting of a sample fluid (e.g., whole blood, cell extract, etc.), a reagent fluid (e.g. high-salt fluid to adjust stringency), a wash fluid (e.g., water), a labeled probe (e.g., nucleic acid or antibody) and/or a detection fluid (e.g., calorimetric or luminogenic substrate), preferably when the multi-substrate chip is in a substantially horizontal position (i.e., no more than ±15 degrees from horizontal, more typically no more than ±8 degrees from horizontal, and most typically no more than ±3 degrees from horizontal). In a further step, it is contemplated that at least one of the plurality of substrates binds an analyte from the fluid (e.g., sample fluid), wherein binding of the analyte is detected in a substantially horizontal position.

Therefore, in particularly contemplated aspects of the inventive subject matter, preferred devices will include a first light source that illuminates one or more reference markers, wherein illumination of the reference markers is employed to determine the focal plane of the optical device (typically a confocal microscope) that analyses the multi-substrate chip. Once the correct focal plane is determined, analysis of the probes, samples, or other molecules on the multi-substrate chip may then proceed without further focusing by using a second light source (typically from the confocal microscope). Such predetermination of the focal plane is particularly advantageous where relatively large numbers of individual measurements are employed. Thus, it should be recognized that analysis of a plurality of substrates on a multi-substrate chip may be performed significantly faster than with known devices since re-focusing from one substrate to the next to optimize signal strength may be omitted. Moreover, it should be recognized that determination of the focal plane using reference markers on the multi-substrate chip (preferably using an illumination wavelength other than the wavelength for illumination of the substrates) will advantageously reduce, if not eliminate photo-bleaching of fluorophores. While it is generally preferred that illumination of the reference marker(s) is performed with a light-emitting diode, other light sources (incandescent or fluorescent) are also considered appropriate. Furthermore, where appropriate, first and second light source may be identical.

Thus, specific embodiments and applications of improved substrate chips devices have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. An analytical device comprising:

a housing at least partially enclosing a multi-substrate chip, wherein the multi-substrate chip includes a gel matrix that comprises a light-blocking material, wherein at least two positional markers and a plurality of substrates are coupled to the gel matrix, and wherein the gel matrix comprises a material selected from the group consisting of agarose, gelatin, and polyacrylamide;

wherein the housing is configured to allow illumination of the at least two positional markers from a first position above the gel matrix by a first light source at a first angle such that two reference signals are produced;

wherein the housing is further configured to allow illumination of a labeled analyte bound to at least one of the plurality of substrates from a second position above the matrix by a second light source at a second angle such that an analyte signal is produced, wherein the first angle and the second angle are not identical;

wherein the positional markers are configured to produce first fluorescence signals and wherein the labeled analyte is configured to produce a second fluorescence signal;

wherein the at least two reference markers and each of the plurality of substrates are disposed on the multi-substrate chip in predetermined spatial relationships to each other to allow determination of a correct focal plane for each of the plurality of substrates;

wherein the housing is still further configured to allow acquisition of the reference signals and the analyte signal when the multi-substrate chip is in a substantially horizontal position;

wherein the multi-substrate chip is disposed within an open cavity that is at least partially formed by the housing, and wherein the cavity has a predetermined volume of between 0.01 ml and 10 ml; and wherein the open cavity is configured to allow reagent addition and illumination of at least one of the plurality of substrates from a point outside the housing without passing through a wall of the housing or without passing through a channel that connects the open cavity with an outside of the housing.

2. The analytical device of claim 1 wherein at least a portion of the housing is translucent.

3. The analytical device of claim 1 wherein the housing is configured to allow illumination of the at least two positional markers in a darkfield.

4. The analytical device of claim 1 further comprising a third positional marker.

5. The analytical device of claim 1 wherein the housing is configured to allow illumination at a difference between the first angle and the second angle of at least 45 degrees.

6. The analytical device of claim 1 further comprising at least one of a barcode, a standard, and a registration marker.

7. The analytical device of claim 1 further comprising an overflow compartment, wherein the open cavity and the overflow compartment are configured such that the open cavity is in fluid communication with the overflow compartment when the open cavity contains a liquid in a volume that is greater than the predetermined volume.

8. The analytical device of claim 1 wherein the housing includes a base element that is configured to transfer at least one of thermal energy and ultrasound energy to at least one of the multi-substrate chip and a fluid disposed in the cavity.

9. The analytical device of claim 1 wherein at least one of the plurality of substrates has a structure that allows binding of an analyte from a sample fluid, and wherein the housing is configured to allow detection of binding of the analyte when the multi-substrate chip is in the housing and in a substantially horizontal position.

10. An analytical device comprising:

a housing having at least one open cavity, and a multi-substrate chip at least partially disposed in the open cavity;

wherein the multi-substrate chip includes a gel matrix that comprises a light-blocking material, wherein a plurality of substrates and at least two positional markers are coupled to the gel matrix, and wherein the gel matrix comprises a material selected from the group consisting of agarose, gelatin, and polyacrylamide;

wherein each of the substrates and positional markers are in predetermined positions relative to each other such as to allow determination of a correct focal plane for each of the substrates, wherein at least one of the plurality of substrates is non-covalently coupled to a carrier in a predetermined position via a crosslinker that is disposed in the gel matrix; and wherein the open cavity is configured to allow reagent addition and illumination of at least one of the plurality of substrates from a point outside the housing without passing through a wall of the housing or without passing through a channel that connects the open cavity with an outside of the housing.

11. The analytical device of claim 10 wherein the matrix is formed from at least two distinct agarose layers.

12. The analytical device of claim 10 wherein the matrix comprises at least one additive selected from the group consisting of a buffer, a humectant, and a surfactant.

13. The analytical device of claim 10 wherein the crosslinker comprises a molecule that binds biotin with a $K_D$ of no greater than $10^{-5}$M.

14. The analytical device of claim 10 further comprising a base element coupled to the housing, wherein the housing has a first width and the base element has a second width, and wherein the first width is smaller than the second width.

15. The analytical device of claim 14 wherein the base element has a lateral cutout in the base element that is configured to operate as a guide element.

16. The analytical device of claim 10 wherein the housing is configured to allow contacting of the plurality of substrates with at least one fluid selected from the group consisting of a sample fluid, a reagent fluid, a wash fluid, and a detection fluid when the multi-substrate chip is in a substantially horizontal position.

17. The analytical device of claim 16 wherein at least one of the plurality of substrates has a structure that allows binding of an analyte from a sample fluid, and wherein binding of the analyte is detected when the multi-substrate chip is in a substantially horizontal position.

18. A magazine comprising a plurality of analytical devices according to claim 1 or claim 10, wherein the plurality of analytical devices are stacked such that a base element of a first device is located above a housing of a second device.

* * * * *